US011055671B1

(12) United States Patent
Rose et al.

(10) Patent No.: US 11,055,671 B1
(45) Date of Patent: Jul. 6, 2021

(54) SYSTEM FOR AND METHOD OF MANAGING CORROSION

(71) Applicant: Government of the United States, as represented by the Secretary of the Air Force, Wright-Patterson AFB, OH (US)

(72) Inventors: David Rose, Ava, NY (US); Matthew J. Rothgeb, Springfield, OH (US); Douglas S. Dudis, Tipp City, OH (US); Nicholas S. Wilson, Springboro, OH (US); Douglas C Hansen, Dayton, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 371 days.

(21) Appl. No.: 16/211,448

(22) Filed: Dec. 6, 2018

(51) Int. Cl.
*G06Q 10/00* (2012.01)
*G01W 1/02* (2006.01)
*G01N 33/00* (2006.01)

(52) U.S. Cl.
CPC ......... *G06Q 10/20* (2013.01); *G01N 33/0075* (2013.01); *G01W 1/02* (2013.01)

(58) Field of Classification Search
None
See application file for complete search history.

(56) References Cited

U.S. PATENT DOCUMENTS

2019/0156598 A1* 5/2019 Palmer, Jr. ........... G07C 5/0808

OTHER PUBLICATIONS

Hoppe et al., AFRL-ML-WP-TR-2001-4162, "Automated Corrosion Detection Program", 2001, University of Dayton Research Institute (Year: 2001).*
Demo et al. "Deployment of a wireless corrosion monitoring system for aircraft applications," 2013 IEEE Aerospace Conference, Big Sky, MT, 2013, pp. 1-10 (Year: 2013).*
Rose, D., A Cumulative Damage Approach to Modeling Atmospheric Corrosion of Steel, University of Dayton, 2014.
Rose, D., Environmental Corrosion Damage Modelling, http://www.afcpo.com/assets/david-rose-rosetrack-2-1445-2017-air-force-corrosion-conference.pdf.
Craig, B., Corrosion Prevention and Control: A Program Management Guide for Selecting Materials, http://www.acqnotes.com/Attachments/Corrosion%20Prevention%20and%20Control%20A%20Program%20Management%20Guide%20for%20Selecting%20Materials.pdf, 2006.
Rose, D., Cumulative Atmospheric Corrosion Damage Modeling of Steel: An Update, 2015.
Rose, D., Enhancements and Extension of the Cumulative Corrosion Damage Modeling Methodology, DoD Corrosion Conference, 2017.
Rose, D., Supercomputer Optimization of Variable Environmental Severity Cumulative Corrosion Damage Models.
Rose, D., Cumulative Corrosion Damage Modeling, ASIP conference, 2016.
Rose, D., Predicting Atmospheric Corrosion Rates for 1010 Steel using a Cumulative Damage Approach.

* cited by examiner

*Primary Examiner* — Roy Y Yl
(74) *Attorney, Agent, or Firm* — AFMCLO/JAZ; Timothy M. Barlow

(57) ABSTRACT

In accordance with various embodiments of the disclosed subject matter, a system and method is configured for generating maintenance events in response to threshold levels of accumulated corrosive stresses experienced by assets or components thereof based on environmental and weather data correlated to respective locations visited and a model of corrosive susceptibility of the assets or components thereof.

19 Claims, 5 Drawing Sheets

SYSTEM FOR AND METHOD OF MANAGING CORROSION

GOVERNMENT INTEREST

The invention described herein may be manufactured and used by or for the Government of the United States for all governmental purposes without the payment of any royalty.

CROSS-REFERENCE TO RELATED APPLICATION

This application claims the benefit of and priority to prior filed Provisional Application Ser. No. 62/595,372, filed Dec. 6, 2017, entitled WEATHER INSTRUMENTATION AND SPECIALIZED ENVIRONMENTAL MONITORING PLATFORM, which is incorporated herein by reference in its entirety.

FIELD OF THE DISCLOSURE

The present disclosure relates generally to systems and methods for determining accumulated corrosive stresses and, more particularly, to determining accumulated corrosive stresses experienced by an asset or component thereof and adapting maintenance procedures and the like in response.

BACKGROUND

Currently, models to predict corrosion and degradation of materials due to environmental exposure are useful to make predictions for narrow geographic regions and for a narrow range of environmental conditions. The experimental measurements used to calibrate such models are typically long-term weight change measurements combined with long-term measurements of chloride deposition and/or sulfur dioxide levels. As a result, such (time-based) models are only capable of making predictions for lengthy periods of time (e.g., a year). A consequence of using such long-term measurements is that these legacy models are incapable of explicitly accounting for the actual underlying chemical and physical mechanisms and processes leading to material degradation.

To better manage maintenance schedule changes there have been efforts to more precisely determine the environmental impact to maintained assets by modeling the environmental conditions to which the assets are exposed. Further, these legacy models cannot be used to ascertain the corrosive attack on assets such as aircraft that routinely move from place-to-place.

SUMMARY OF THE INVENTION

Various deficiencies in the prior art are addressed below by the disclosed systems, methods, architectures, mechanisms, apparatus, computer implemented method and/or framework configured for generating maintenance events in response to threshold levels of accumulated corrosive stresses experienced by assets or components thereof based on environmental and weather data correlated to respective locations visited and a model of corrosive susceptibility of the assets or components thereof.

Specifically, various embodiments contemplate receiving time-stamped weather and contaminant data from one or more of a plurality of environmental monitoring platforms (EMPs) dispersed at respective locations and configured to periodically gather local weather condition and atmospheric contaminant measurements to generate thereby time-stamped weather and contaminant data. Each of the assets or components thereof is associated with a respective accumulated corrosion damage profile (ACDP) defining respective accumulated amounts of exposure. Each ACDP is updated in accordance with weather and contaminant data correlating to time-location data associated with the respective asset. The ACDP of each asset may be used to modify asset tasking to accommodate changes in maintenance scheduling, performance envelope, asset siting/storage and the like. For example, maintenance schedules associated with an airframe or other asset may be adapted in response to the proximity of the home airbase associated with the plane to an ocean or other salt water body. That is, the duration between scheduled maintenance procedures of an asset or portion thereof may be shortened by some amount depending upon the distance of the home airbase to the salt water body by, illustratively, 10% if within a first distance or 20% if within a second (shorter) distance.

The environmental, weather, and chloride data are co-located, high resolution, and automatically formatted and sent to a database for near-to-real-time access to field conditions. Thus, a corrosion damage model may be constructed with high confidence based on actual site conditions with very little lag time. The centralized data logger combines, formats, time stamps, and transmits all data remotely with no need for user interaction outside of the collection and analysis of filters for chloride levels and characterization. Alternatively, instrumentation for real time chloride data may be incorporated as well as numerous other types of equipment and sensors for any other weather or atmospheric condition.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
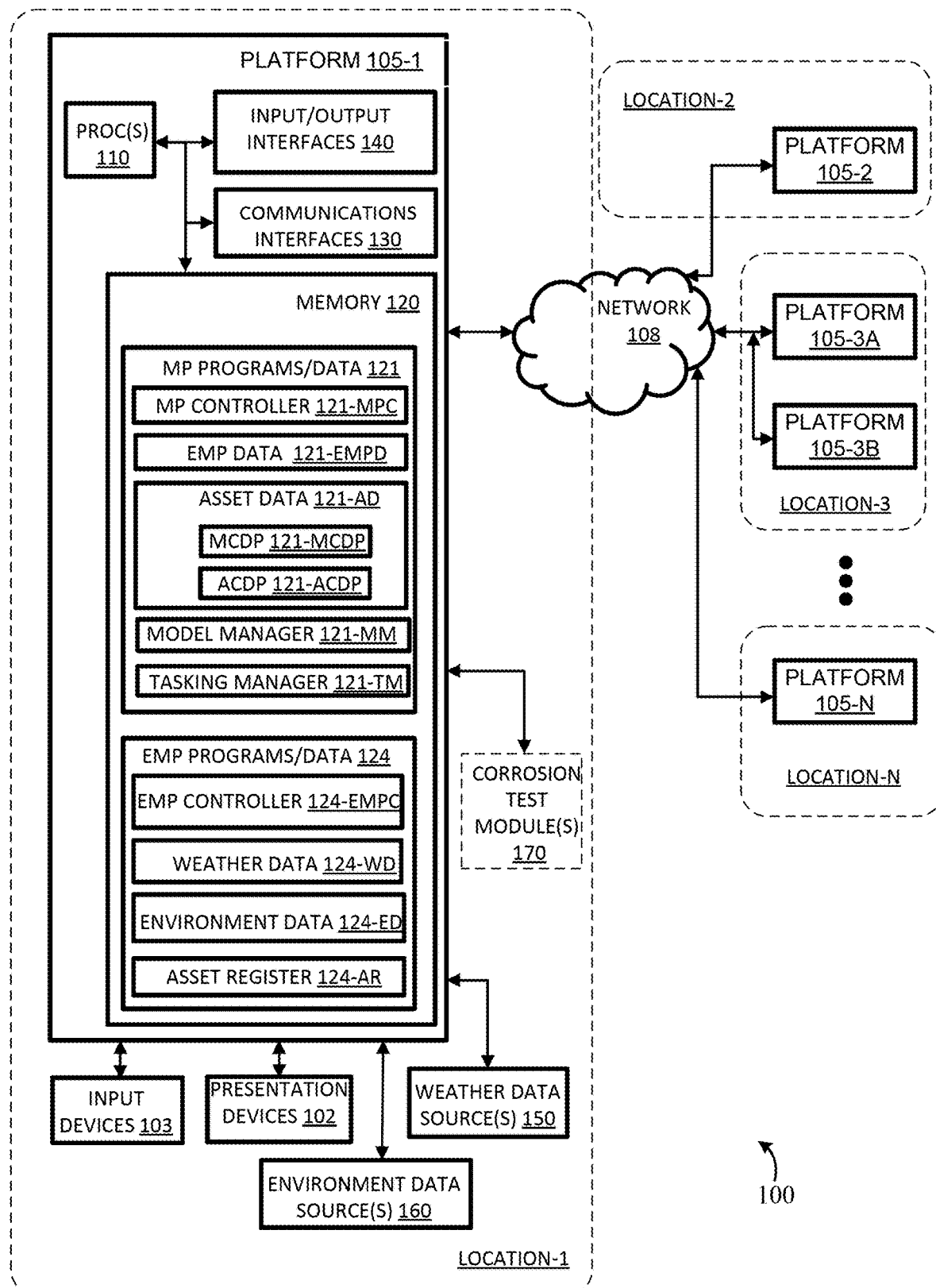
FIG. 1 depicts a high-level block diagram of a system according to an embodiment.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

Various embodiments discussed herein comprise, illustratively, systems, methods, architectures, mechanisms, apparatus, computer implemented methods and/or frameworks configured for determining accumulated corrosive stresses experienced by assets or components thereof, such as airplanes, ground vehicles, infrastructure and other equipment or components thereof. Of particular interest is the accurate tracking of the specific corrosive stresses experienced by mobile assets at each of the different ground locations where the mobile asset may be located for a period of time, e.g. hours, days, months, etc. Such ground locations may comprise airbases with very different environments, for example environments having differing weather patterns, or near saltwater bodies, or in dusty/desert environments, or subjected to extreme cold or heat, or located at high or low elevations, or proximate sources of industrial pollutants or other sources of caustic contaminants. Generally speaking, the environment within which an asset or components thereof may be located for some period of time may be associated with greater or lesser amounts of any of temperature, pressure, humidity and insolation, and/or exposed to any of a variety of atmospheric contaminants such as chlorides, ozone, sulfur dioxide and so on.

FIG. 1 depicts a high-level block diagram of a system according to an embodiment. Specifically, the system 100 of FIG. 1 comprises one or more data processing elements, computing devices, network elements and the like cooperating as described herein to implement various embodiments. Not all of the described data processing elements, computing devices, network elements and the like are necessary to implement each embodiment. The exemplary system 100 described herein is provided for illustrative purposes only.

Referring to FIG. 1, each of a plurality of locations denoted as LOCATION-1, LOCATION-2, LOCATION-3 and so on through LOCATION-N (e.g., airbases, airports, testing facilities or other locations or portions thereof) has associated with it a respective environmental monitoring platform (EMP) 105. As depicted in FIG. 1, first platform 105-1 comprises a combined environmental monitoring platform (EMP) and management platform (MP) at first location LOCATION-1. That is, first platform 105-1 comprises a platform including both EMP functionality (i.e., EMP programs/data 124) and MP functionality (i.e. MP programs/data 121) as will be described in more detail below. As depicted in FIG. 1, second platform 105-2 comprises a platform including EMP functionality at second location LOCATION-2, third platforms 105-3A and 105-3B comprise platforms including EMP functionality at different areas/locations within third location LOCATION-3 and so on up to Nth platform 105-N which comprises a platform including EMP functionality located within Nth location LOCATION-N.

As depicted in FIG. 1, each of platforms 105-1 through 105-N performs various EMP functions such as periodically gathering local weather condition and atmospheric contaminant measurements to generate thereby time-stamped weather and contamination data associated with the respective location.

As depicted in FIG. 1, combined EMP/MP platform 105-1 performs various management functions such as utilizing the time-stamped weather and atmospheric contaminant data provided by the various platforms 105 to update accumulated corrosion damage profiles associated with assets of interest or portions thereof, determine corrosion damage levels and/or perform various optional functions such as invoking/adapting asset maintenance procedures, re-tasking assets, relocating assets and the like.

To simplify the discussion, the EMP functions as well as MP functions will be discussed within the context of first platform 105-1. However, it will be appreciated by those skilled in the art that the EMP functions described herein are the same for each of the platforms 105, that any of the platforms 105 may comprise a combined EMP/MP platform and therefore perform one or both of the EMP/MP functions described herein with respect to first platform 105-1. Further, the various MP functions described herein may be performed by different entities such as servers, management systems, logistics management systems or other relevant local or remote system (not shown) suitable for use in performing the MP functions as described herein. Such local measurement equipment may comprise any of local weather equipment, local atmospheric contaminant equipment, local defense sensor equipment, transient equipment (e.g., sensors on assets passing through a location) and so on.

As shown in FIG. 1, the platforms 105 are configured in a particular manner in terms of hardware, software, input/output resources, connected devices/functions and the like. However, it will be appreciated by those skilled in the art that the platforms 105 may be configured according to any one of a number of computing topologies or configurations. That is, any of the platforms 105 may comprise a general purpose computer, a special purpose computer, a specific type of server and/or any other computing device capable of performing the various functions described herein. Thus, the platforms 105 as described herein with respect to FIG. 1 may also be implemented as a general purpose computing device.

As depicted in FIG. 1, each platform 105 includes one or more processors 110, a memory 120, a communications interface 130 and an input/output (I/O) interface 140. The processor 110 is coupled to each of memory 120, communication interface 130, and I/O interface 140.

The processor 110 is configured for controlling the operation of the platform 105, including operations supporting the methodologies described herein with respect to the various figures.

The memory 120 is configured for storing information suitable for use in performing the various functions described herein according to the various embodiments. Specifically, memory 120 may store management platform programs/data 121 to implement various MP functions and/or environmental monitoring platform programs/data 124 to implement various EMP functions. Within the context of the various embodiments, the programs/data 121 and/or 124 may vary depending upon the specific functions implemented by the platform 105.

Generally speaking, the memory 120 may store any information suitable for use by the platform 105 in implementing one or more of the various methodologies or mechanisms described herein. It will be noted that while various functions are associated with specific programs or databases, there is no requirement that such functions be associated in the specific manner. Thus, any suitable implementations achieving the functions of the various embodiments may be used.

The communications interfaces 130 may include one or more services signaling interfaces such as a Wi-Fi or WiMAX interface, a 3G broadband cellular network wireless interface, a 4G broadband cellular network wireless interface, an Ethernet interface and the like for supporting data/services signaling between platform 105, network 108, weather data sources 150, environmental data sources 160 and/or other entities interacting with the platform 105. It will be appreciated that fewer or more, as well as different, communications interfaces may be supported. The various communications interfaces 130 are adapted to facilitate the transfer of files, data, messages, requests and the like between various entities in accordance with the embodiments discussed herein.

The I/O interface 140 may be coupled to one or more presentation devices (PDs) 102 such as associated with display devices for presenting information to a user, one or more input devices (IDs) 103 such as computer display, touch screen or keypad input devices for enabling user input, and/or interfaces enabling communication between the platform 105 and other computing, networking, presentation or input/output devices (not shown).

Presentation devices 102 may include a display screen, a projector, a printer, one or more speakers, and the like, which may be used for displaying data, displaying video, playing audio, and the like, as well as various combinations thereof. The typical presentation interfaces associated with user devices, including the design and operation of such interfaces, will be understood by one skilled in the art. In various embodiments, the presentation devices 102 used to display information pertaining to the various methodologies. In various embodiments, the presentation devices are not utilized; rather, output/presentation information pertaining to the various methodologies is transmitted to a remote server or other external resource (not shown).

Input devices 103 may include any user control devices suitable for use in enabling a local or remote user of the platform 105 to interact with functional modules implemented at the platform 105. For example, the input devices 103 may include touch screen based user controls, stylus-based user controls, a keyboard and/or mouse, voice-based user controls, and the like, as well as various combinations thereof. The typical user control interfaces of user devices, including the design and operation of such interfaces, will be understood by one skilled in the art. In various embodiments, the input devices 103 are not utilized; rather, input/control information pertaining to the various methodologies is received from a remote server or other external resource (not shown).

Although primarily depicted and described as having specific types and arrangements of components, it will be appreciated that any other suitable types and/or arrangements of components may be used for platform 105.

It will be appreciated that the functions depicted and described herein may be implemented in software and/or hardware, e.g., using a general purpose computer, one or more application specific integrated circuits (ASIC), and/or any other hardware equivalents. In one embodiment, the various programs depicted as loaded within memory 120 are executed by the processor(s) 110 to implement their respective functions. It will also be appreciated that the various programs may be stored on a computer readable storage medium prior to being loaded into memory 120; such computer readable storage media comprising semiconductor memory devices, magnetic media, optical media, electromagnetic media and the like. Generally speaking, any form of tangible computer memory may be used to store computer instructions which, when executed by the processor 110, operate to perform the various methods and functions described herein.

It is contemplated that some of the steps discussed herein as software methods may be implemented within hardware, for example, as circuitry that cooperates with the processor to perform various method steps. Portions of the functions/elements described herein may be implemented as a computer program product wherein computer instructions, when processed by a computer, adapt the operation of the computer such that the methods and/or techniques described herein are invoked or otherwise provided. Instructions for invoking the inventive methods may be stored in tangible fixed or removable media, transmitted via a data stream in a broadcast or other tangible signal-bearing medium, and/or stored within a memory within a computing device operating according to the instructions.

EMP Functions

As depicted in FIG. 1, the programs/data portion 124 of memory 120 of each EMP-function platform 105 includes EMP-related functional modules denoted as follows: EMP controller 124-EMPC, weather data 124-WD, environmental data 124-ED and an optional asset register 124-AR.

The EMP controller 124-EMPC provides a mechanism to manage the collection and storage of local weather information and environmental information, as well as the transmission toward a management platform of time-stamped local weather and environmental information collected by the EMP function implemented at a platform 105.

Local weather information may be received from weather data sources 150 associated with the relevant location, such as weather instrumentation integrated into, connected to or otherwise associated with the EMP platform 105. The weather data sources 150 may comprise nearby weather monitoring stations/services, such as weather stations/services associated with an airfield or location proximate an airfield. Generally speaking, the weather data sources 150 may comprise any source of weather related data useful in characterizing the weather conditions associated with the location.

In various embodiments, the weather data source 150 may comprise a commercially procured weather station configured to collect data such as temperature, relative humidity, air pressure, rainfall, rain intensity, windspeed (average, maximum, minimum), wind direction and/or other weather related information.

Local environmental information may be received from local environmental data sources 160 associated with the relevant location, such as in ambient air quality monitor, a chloride deposition monitor and/or other monitors of airborne contaminants relevant to the corrosion or degradation of assets or components thereof. The ambient air quality monitor may comprise a commercially procured system consisting of several complex instruments used to detect gaseous pollutants in the atmosphere. The system may be modular in that a variety of sensors may be added to the platform if so desired depending upon the type of pollutant to be monitored and the value of the data to be procured thereby. The chloride deposition monitor may comprise a plurality of filter cartridges and solenoid valves with a flow controller and data logger configured to allow each filter to be exposed to air brought in from the outside individually, wherein the controller is programmed to allow for air to be collected over any time duration of interest. In some embodiments it is contemplated that a weekly collection of atmospheric chloride deposition data is sufficiently accurate. In other embodiments more or less frequent collection of atmospheric or deposition data is employed. In various embodiments where filters are manually collected for analysis a triggering signal is generated by the EMP controller 124-EMPC to indicate that such collection is due.

The EMP controller 124-EMPC is configured to collect weather data from one or more weather data sources 150, time stamp the retrieved weather data, and store it as weather data 124-WD. The EMP controller 124-EMPC is configured to collect environmental data from one or more environmental data sources 160, time stamp the retrieved environmental data, and store it as environmental data 124-ED.

The EMP controller 124-EMPC is configured to retrieve weather data 124-WD and environmental data 124-ED and provide this data to a requesting system such as a management platform 105. In various embodiments, the collected weather and environmental data is periodically transmitted to a management platform, central server or data repository. In various embodiments, the collected weather and environmental data are transmitted to a management platform, central server, or data repository in response to a request received therefore.

The EMP controller 124-EMPC is optionally configured to retrieve information pertaining to asset ingress or egress at the relevant location (e.g., an airplane or vehicle entering or leaving a location). Specifically, in various embodiments the EMP controller 124-EMPC may be connected to local or regional flight control or asset management resources to receive therefrom information indicative of when an identified asset entered the location and when the identified asset exited the location such that time-location data associated with an asset or portion thereof may be accumulated by an EMP platform directly. In these embodiments, available asset ingress/egress may be communicated to a management platform for further processing such as described below.

MP Functions

As depicted in FIG. 1, the programs/data portion 121 of memory 120 of each MP-function platform 105 includes MP-related functional modules denoted as follows: MP controller 121-MPC, EMP data 121-EMPD, asset data 121-AD, an optional model manager 121-MM and an optional tasking manager 121-TM.

The MP controller 121-MPC provides a mechanism to manage the correlation of asset time-location data with time-stamped weather and environmental data from each of a plurality of locations such that an accurate determination of a corrosive "load" imparted to the asset or components thereof at each of the locations visited by the asset may be individually assessed and added to a respective accumulated corrosive "load" experienced by the asset or component thereof. In this manner, an accurate determination of the likely accumulated degradation or corrosion of each asset or components thereof may be determined and appropriate corrective action, maintenance action, and/or re-tasking/repurposing/repositioning of the asset may be performed.

The MP controller 121-MPC is configured to receive time-stamped weather and environmental data from platforms 105 implementing the EMP functions described above with respect to EMP programs/data 124, which is stored as EMP data 121-EMPD.

The MP controller 121-MPC is configured to store asset data 121-AD associated with any asset or asset component of interest and may comprise, illustratively, time-location data associated with each asset, a model corrosion damage profile (MCDP) 121-MCDP associated with each asset or component thereof and an accumulated corrosion damage profile (ACDP) 121-ACDP associated with each asset or components thereof.

Each asset, and therefore each component of that asset, is associated with time-location data which may be stored as part of a time-location profile (TLP) used to identify where an asset has been (e.g., ground locations), when the asset arrived at a location, and when the asset departed the location. For example, an airplane may have been at a first airfield (location 1) for several weeks (time period 1), then prepped for flight while waiting for two hours (time period 2) in a high exhaust portion (location 1-A) of the first airfield before flying to a second airfield (location 2) where it sat for a week (time period 3). Each of these locations/time periods is associated with respective local weather conditions, atmospheric contaminants and the like which imparted a particular corrosive load to the asset during the time the asset was at that location. The time-location data may be received from the asset itself, from flight control/management systems interacting with the asset as it moves from location to location, from airfield/airports or other locations where the asset visits and so on.

Each asset or component thereof has associated with it a respective model corrosion damage profile (MCDP) which is used to store information indicative of the response of an asset or component thereof to various weather conditions, atmospheric contaminants and/or other corrosive loading imparted thereto. The MCDP may comprise a model which takes into account the individual and/or combined corrosive impact to the asset or component thereof of weather conditions, atmospheric contaminants and the like. The MCDP may comprise a profile indicative of threshold event reporting levels (e.g., "acceptable," "warning," "critical," "dangerous" etc.) associated with instantaneous or accumulated corrosive loads. Generally speaking, the MCDP may be used to store data indicative of a level of individual and/or combined exposure to various weather conditions, atmospheric contaminants and the like which have been determined to impart a corrosive stress or other degradation upon the particular asset or component thereof. For example, the MCDP may identify threshold event reporting levels associated with the impact upon an asset or component thereof over time, temperature, pressure etc. due to specific chemical or physical effects such as chloride, ozone, sulfur dioxide and other chemical exposures, temperature, relative humidity, insolation and so on. The MCDP may be implemented as any type of data structure or format suitable for use within the context of the management platform, such as via database fields, defined packet structures and the like. The information stored in the MCDP may be based upon design/specification criteria, materials selection, and/or asset resiliency modelling, determined in accordance with prior operational data or any combination thereof. Further, the MCDP may be adapted over time as improved information becomes available, as will be discussed below with respect to an optional model manager 121-MM.

Each asset or component thereof has associated with it an accumulated corrosion damage profile (ACDP) which is used to store data indicative of a respective accumulated amount of exposure to each of a plurality of weather conditions, atmospheric contaminants and the like which have been determined to impart or contribute to a corrosive stress or other degradation upon the particular asset or component thereof, such as those included within the MCDP. The ACDP may be implemented as any type of data structure or format suitable for use within the context of the management platform, such as via database fields, defined packet structures and the like.

The MP controller 121-MPC is configured to update the ACDP of each asset or component using received EMP data that correlates or coincides with time-location information associated with the asset. In this manner, an accumulated corrosive impact imparted to an asset or components thereof is maintained as part of the asset data 121-AD.

The MP controller 121-MPC is configured to generate event information pertaining to ACDP information indicative of weather and/or environmental exposure to the asset or component thereof exceeding, illustratively, one or more threshold levels. The particular threshold levels may be indicated via the corresponding MCDP or in some other manner. The event information may be transmitted to a remote asset management entity. The event information is useful in determining whether a maintenance procedure should be performed upon the asset or component thereof. The event information is useful in determining whether a maintenance schedule should be adapted in some way (e.g., a duration between procedures might be reduced in response to excessive exposure to dust, salt, chlorides, temperature extremes, rain, and/or other factors as discussed herein either individually or in any combination). The specific changes in maintenance schedule depend upon the specific asset or components thereof, the specific corrosive load imparted thereto, the tolerance of the asset or components thereof with respect to the corrosive load, and so on.

In various embodiments, an optional tasking manager 121-TM uses event information, asset data and the like to generate tasking or re-tasking orders associated with an asset. For example, the tasking manager 121-TMA directs changes in maintenance procedures as described herein, changes in mission or disposition of an asset if possible, redeployment of an asset, and so on.

In various embodiments, an optional model manager 121-MM evaluates additional data pertaining to the impact of corrosive loads on assets or components thereof to adjust the MCDP in response to newly gained information. Such information may comprise unexpectedly high or low corrosion associated with one or more weather or environmental factors, either alone or in combination. Such information may comprise revised projections from a manufacturer of an asset or component thereof. Generally speaking, the model manager 121-MM is configured to adjust the corrosion model associated with an asset or components thereof such that a more precise evaluation may be made with respect to individual and accumulated corrosive loading.

In various embodiments, post-event processing of an asset of component thereof includes a respective analysis to determine a remaining service life, condition or other information related to whether the asset or component thereof could have been left in service longer or should have been removed from service sooner. This information may be used for several purposes, including adapting the various models associated with the asset or component thereof, such as described below with respect to the method 300 of FIG. 3.

Thus, various embodiments contemplate an EMP in which sources of environmental, weather and chloride data are co-located, provide high resolution data, automatically format the data and send the data to a local and/or remote database to provide thereby near to real time access to field conditions. Thus, a corrosion damage model may be constructed with high confidence based on actual site conditions with very little lag time. A centralized data logger combines, formats, time stamps and transmits all data remotely with no need for user interaction outside of the collection and analysis of filters for chloride levels and characterization (other than user interaction as might be required of specialty data collection components as described herein with respect to the various embodiments). Various embodiments further contemplate a platform real time chloride data acquisition functions as well using appropriate instruments.

Optionally, various embodiments of the platform 105 may be used to collect data about actual corrosion test site environmental conditions via, illustratively, one or more corrosion test modules (CTM) 170 operably coupled to a platform 105 (e.g., via a cellular telephone or other interface) to provide thereto near-to-real time corrosion damage data associated with a specific site that be studied and utilized in modeling as well as in advanced laboratory environmental test chambers. Test stand and sample racks may hold samples that are exposed in that environment and can be studied after exposure wherein the data informs the user to what the test specimens have been exposed while at the test site.

Figure 2:
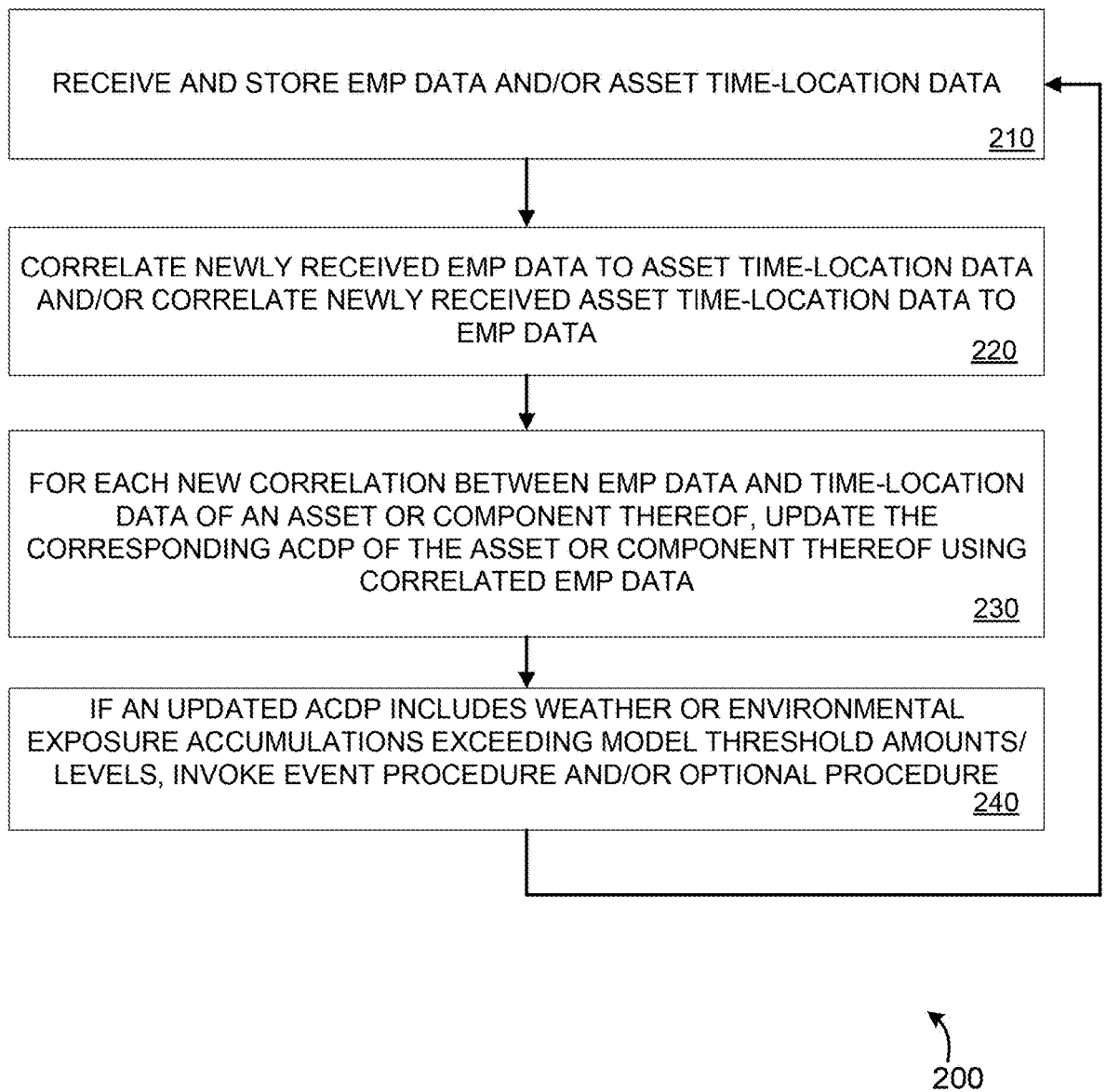
FIG. 2 depicts a process workflow diagram of management platform operations according to an embodiment.

FIG. 2 depicts a process workflow diagram of management platform operations according to an embodiment. Specifically, FIG. 2 depicts a flow diagram of a method suitable for use by, illustratively, the MP controller 121-MPC described above with respect to the system 100 of FIG. 1.

At step 210, the MP receives time-stamped weather and environmental contaminant data associated with one or more of a plurality of environmental monitoring platforms (EMPs) and/or time-location data associated with one or more of a plurality of assets or components thereof; the received data is stored in memory 120.

At step 220, any newly received EMP data is correlated to new or existing asset time-location data, and any newly received asset time-location data is correlated to new or existing EMP data At step 230, for each new correlation between EMP data and time location data of an asset or components thereof, the accumulated corrosion damage profile (ACDP) of the asset or component thereof is updated in accordance with the respective correlating EMP data.

At step 240, if an updated ACDP includes weather or environmental exposure accumulations exceeding model threshold amounts, invoked an event procedure and/or optional procedure. That is, in the case of an indication of an asset or components thereof having experienced whether or environmental corrosive loading exceeding a maximum amount as determined by a model or other criteria, an event procedure is invoked whereby an indication of the condition is transmitted to a maintenance or other management system. Optionally, a procedure such as retasking may also be invoked.

In various embodiments, the model used for any particular asset or components thereof is based upon, or incorporates the time-dependent, material-property-specific features of, the Cumulative Corrosion Damage Model (CCDM) described in D. H. Rose, "A Cumulative Damage Approach to Modeling Atmospheric Corrosion of Steel", Ph.D. Dissertation," University of Dayton, 2014. In various embodiments, other cumulative corrosion damage models or CCDM frameworks are utilized, such as those discussed in any of the following publications and/or modifications thereof:

Rose, D. H. and McCombie, S. J., "*Enhancements and Extension of the Cumulative Corrosion Damage Modeling Methodology*", DoD and Allied Nations Corrosion Conference, 2017; Rose, D. H. and McCombie, S. J., "*Environmental Cumulative Corrosion Damage Modeling*", Air Force Corrosion Conference, 2017; Rose, D. H. and McCombie, S. J., *Cumulative Corrosion Damage Modeling: A Novel Approach to Evaluating Environmental Attack on Aerospace Alloys*, Aircraft Structural Integrity Program Conference, 2016; Rose, D. H., McCombie, S. J., Dudis, D. S., Smith, R. A., and Hansen, D. C., "*Cumulative Atmospheric Corrosion Damage Modeling of Steel: An Update*", DoD and Allied Nations Corrosion Conference, 2015; Rose, D. H., Smith, R. A., Dudis, D. S., McCombie, S. J., and Hansen, D. C., "*Supercomputer Optimization of Variable Environmental Severity Cumulative Corrosion Damage Models*", Air Force High Performance Computing (HPC) User Forum, 2015; Rose, D. H., McCombie, S. J., Smith, R. A., Dudis, D. S., and Hansen, D. C., "*Cumulative Corrosion Damage Modeling of Steel: An Update*", DoD Corrosion Forum XXXIV, 2014; Rose, D. H., Hansen, D. C., McCombie, S. J., "*Advanced Environmental Severity Index Based Upon Cumulative Corrosion Damage Modeling*", poster presentation, 2014 ASETS Defense Workshop; Rose, D. H., McCombie, S. J., Angel, J. D., and Hansen, D. C., "*Predicting Atmospheric Corrosion Rates for* 1010 Steel using a Cumulative Damage Approach", Proceedings of the 224th Meeting of the Electrochemical Society, 2013.

The method 200 may be executed periodically or may run continually as EMP or time-location data is generated/received. The method 200 operates to continually update a measure of actual weather/environmental impact to an asset or component thereof. In this manner, an efficient and less wasteful scheduling of maintenance and/or other procedures may be realized without negatively impacting readiness or operational abilities.

Generally speaking, the CCDM used within the context of the various embodiments may be formulated as a framework built around actual chemical and physical effects experienced by an asset or component thereof. Exemplars include, but are not limited to, chloride, ozone, sulfur dioxide and other chemical exposures, temperature, relative humidity, insolation, and their changes with time. Advantageously, the framework may be extended to other factors far beyond those initially examined (i.e., the CCDM is extensible). Also, the above-described methods are not simply time-based; rather, they take into account established chemical and physical processes as actually experienced by the asset or components thereof.

The extensibility of the CCDM encompasses multiple facets. For instance, the CCDM may be adjusted if a particular pollutant, weather condition, or physical effect is present in a specific location. An example might be inclusion of phosphate exposure if a location is near a phosphate production facility, or volcanic gases if subject to exposure to same. Simple time-based methods may require a complete recalibration for every location and site, or categorization of sites into averaged categories.

The superiority of the CCDM derives from its sound scientific underpinnings. This may be understood from two illustrations. Prior art, time-based methods do not capture varying weather patterns. Such a model calibrated only during the cold, dry winter-season for a specific location would be completely devoid of relevant and important corrosion data for the hot, humid seasons. Nonetheless, practice has been to apply such models strictly on time-exposure basis regardless of the variations in the underlying climatic and pollution variations, and this is due to the limitations of such models.

A second superiority of the innovations disclosed herein is that the underlying calibration of the methods may be based on more relevant and reliable measurements than weight loss. In some instances, weight loss is known to derive from more than one mechanism. Prior art models used in prior art which rely on weight loss measurements do not discriminate amongst such mechanisms. The CCDM based framework requires quantitative measurements associated with time based environmental measurements. This allows a more robust approach and more relevant ground-based sensor-derived information.

The CCDM approach offers great advantage in that once a material is calibrated with respect to the underlying physical mechanisms, that calibration is valid regardless of the season of year or geographic location of the application of the method. For instance, if 1010 steel corrosion is calibrated with respect to exposure to humidity and sulfur dioxide, the calibration data is valid regardless of where and when then exposure takes place. This offers broad applicability.

The present invention discloses the utility of developing and applying the CCDM or similar models (hereafter CCDM frameworks to incorporate any such models that might be developed) to asset management. In particular, the CCDM frameworks may be coupled with deployable environmental monitoring systems (also disclosed herein) to provide condition-based asset management.

The deployable environmental monitoring systems advantageously provide an extensible and tailorable to environmental influences of interest. An important element is the transmission of the data to be made available for analysis. In this way, fluctuating environmental conditions specific to sites of interest may be appropriately accounted for. The utility of this advancement may be appreciated by illustrating its application to military aircraft.

Figure 3:
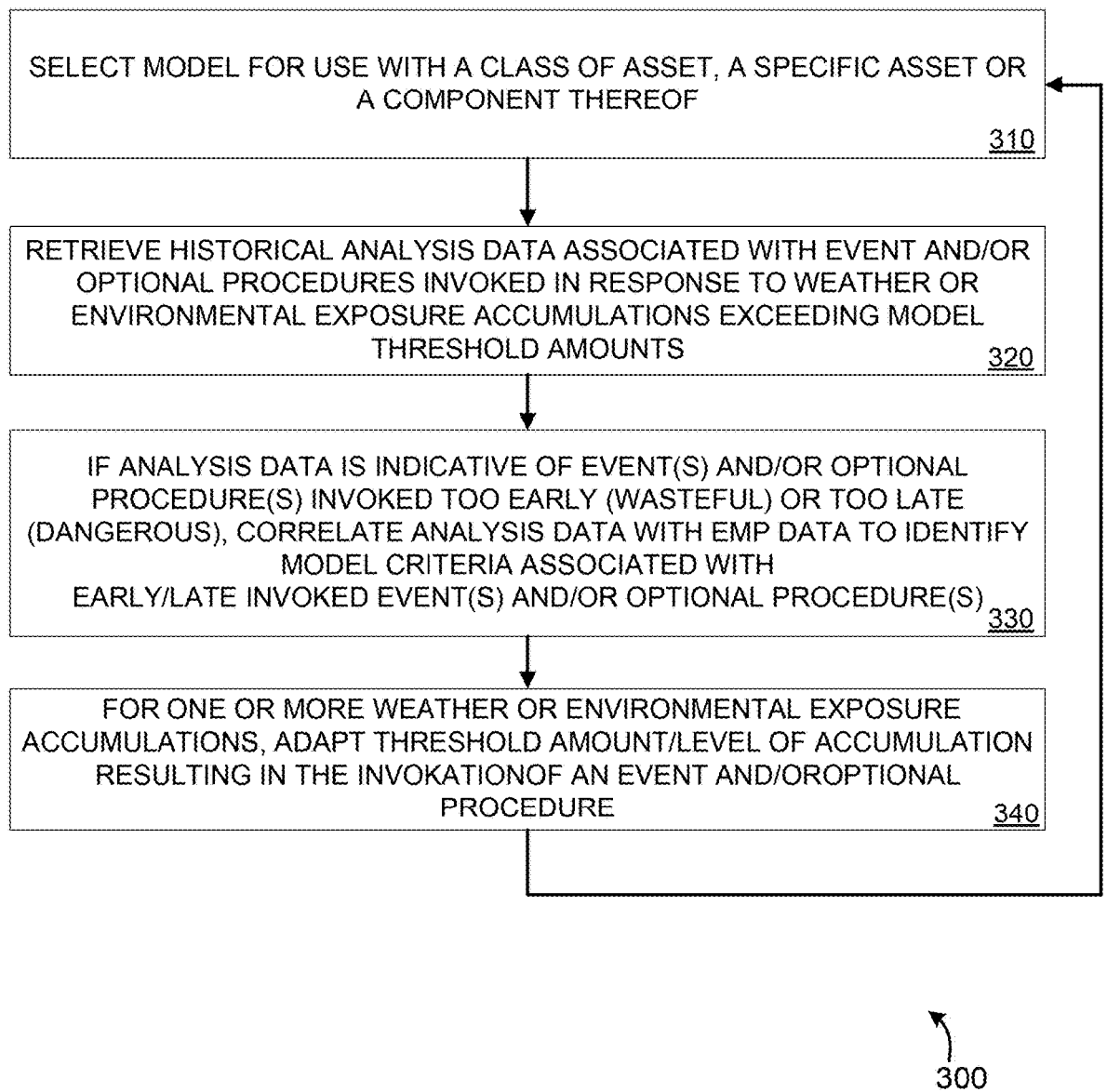
FIG. 3 depicts a process workflow diagram of a model refinement operation according to an embodiment.

FIG. 3 depicts a process workflow diagram of a model refinement operation according to an embodiment. Specifically, FIG. 3 depicts a flow diagram of a method suitable for use by, illustratively, the MP controller 121-MPC described above with respect to the system 100 of FIG. 1.

At step 310, the MP selects a model for use with a class of asset, a specific asset or a component thereof. As noted above, various CCDM models may be used within the framework of the embodiments discussed herein. For example, as previously noted a model corrosion damage profile (MCDP) associated with each asset class, asset or component thereof may be used in conjunction with a respective accumulated corrosion damage profile (ACDP) to identify when relevant thresholds of accumulated exposure to corrosion-related criteria are reached. The MCDP or other model may be determined in accordance with design criteria as well as in accordance with a cumulative corrosion damage model (CCDM). Further, the MCDP and/or CCDM of an asset or portion thereof may be adapted in response to empirical data indicative of corrosion factors outside the CCDM as well as analysis data as described herein.

At step 320, historical analysis data associated with event and/or optional procedures invoked at step 240 of the method 200 of FIG. 2 is retrieved. Such historical analysis data may comprise evaluations of assets or components thereof changed out or inspected during invoked maintenance procedures, further guidance from manufacturers regarding asset/component degradation or wear, further understanding or analysis pertaining to the relevant materials used to manufacture an asset or component thereof and so on. Essentially, any further analysis or information useful in describing the actual or expected post-procedure state of an asset or component thereof may be retrieved.

At step 330, if the retrieved analysis data is indicative of events or optional procedure being invoked too early (e.g., unnecessary maintenance or replacement) or too late (e.g., maintenance or replacement after a safety related operational parameter such has been exceeded) then the analysis data is correlated with the relevant EMP data to identify model criteria most likely associated with the early or late invocation of the event(s) or procedure(s).

At step 340, the model for the asset class, asset or component thereof is modified in response to the correlation, such as by adapting up or down the threshold amount/level of an accumulated weather parameter, environmental parameter, or combination of weather and/or environmental parameters associated with a triggering of an event or optional procedure.

The method 300 may be executed periodically or may run continually as analysis data is generated/received. The method 300 operates to refine the application of the selected CCDM model in accordance with actual weather/environmental impact to an asset or component thereof. In this manner, the accuracy of the model as used for the asset class, asset or component thereof such that a more efficient and less wasteful scheduling of maintenance and/or other procedures may be realized without negatively impacting readiness or operational abilities.

Corrosion in military aircraft is generally believed to be mostly influenced by their exposure to environmental conditions on the ground. Military aircraft often spend extended periods between use, and when in use, it often entails deployments to widely disparate environments. By contrast, commercial aircraft tend to be in regular and constant use, to the greatest extent possible, to enhance their profitability. Various embodiments provide a precise mechanism for precisely determining a cumulative impact to, for example, an aircraft or subsystem/component thereof by utilizing a CCDM framework such as described herein for evaluating the experienced environmental, weather and atmospheric contaminant data of the aircraft or subsystem/component thereof, which data is retrieved from deployed sensor systems may be placed at, illustratively, each air base. This couples the time of the aircraft exposure at a specific location with the actual environmental conditions at that location while the aircraft is there.

The impact of this may be far reaching. A plethora of efforts have attempted to develop corrosion sensors, or corrosion environment sensors, for aircraft. These are for specific subcomponents or systems on the aircraft, and different sensors are used for different aircraft, generally with limited success. By contrast, the innovation disclosed herein allow for the utilization of one ground-based suite of sensors, feeding the resulting environmental information to a CCDM type framework, calibrated to the assets of interest. In other words, one suite of sensors may be used for corrosion management of all the aircraft present at that location, regardless of the type or number of aircraft, as well as ground support equipment and any other assets of interest at the base in question.

Additional corrosion damage occurs when aircraft are exposed to salt water conditions. This may occur while the aircraft are deployed at bases exposed to salt spray and/or high levels of chloride aerosols. Furthermore, aircraft not normally exposed to salt spray in their basing may experience salt spray/chloride aerosol exposure when flying over salt water. An extension of the innovations disclosed herein is the implementation of a limited suite of aircraft-based sensors to account for such exposures. The resulting data may readily be incorporated into the overall corrosion management framework. This is an exemplar of the extensibility of the methods.

One embodiment of a Weather Instrumentation and Specialized Environmental Monitoring Platform (WISE-MP) utilizes several specific consumer off-the-shelf technologies as sub-systems, for example, the initially developed WISE-MP platforms utilize an Airpointer ambient air monitoring system (manufactured by mlu-recordum Environmental Monitoring Solutions GmbH) for monitoring ambient air quality. There are competing systems available on the marketplace to acquire this type of data and/or one could build a system from components to accomplish the same thing. The same applies to the weather station as numerous products are available on the marketplace to gather this type of data. The WISE-MP invention employs a combination of several sub-systems (Ambient Air Quality, Weather, Chloride monitoring, etc.) that are currently not built into a single cohesive system for monitoring critical environmental, weather and atmospheric contaminant data in one package and making that data readily available to users for site-specific analysis and modeling. Additionally the WISE-MP is of robust design and allows for easy integration of other sensor packages in the future if desired. Various embodiments contemplate collecting time of wetness, solar irradiance and the like via local or remote databases, or via local stand-alone sensors.

Numerous local, state, and federal organizations (including the EPA) sponsor sites to collect air pollution and chloride deposition data. Similarly, NOAA, the military services, and other organizations collect weather data. There is a small number of monitoring sites such as those under the EPA's Clean Air Status and Trends Network (CASTNET) that collect multi-parameter outdoor air pollution, chloride deposition, and weather data. However, most existing air pollution monitoring sites are limited to measuring individual or at most a few of these parameters. A further complexity is that sponsoring organizations traditionally conduct air pollution, chloride deposition, and weather data measurement programs for different reasons. As a result, their respective data archiving processes are not integrated. In addition, the existing monitoring sites are normally not placed in the same locations where engineering analyses are needed for design engineering or sustainment purposes. Laboratory-based corrosion testing may be used to screen materials for environmental degradation but data measured during such tests often fails to capture real world effects and behaviors at outdoor locations. As a result, lab measurements are often unsuitable for engineering analysis purposes.

Highly precise equipment used to collect gaseous air pollution data at existing environmental monitoring sites is typically placed in temperature-controlled, non-mobile buildings. Such infrastructure is costly and inflexible. There are commercially available, small-scale ambient air monitoring systems (Airpointer and others) that can accurately measure air pollution levels. Some of these systems also possess the capability to link to compact weather stations and transmit the combined data stream wirelessly to a remote database. However, such systems cannot collect analog data, such as that which acquired from filter pack chloride deposition monitors. In addition, these systems are not extensible, which precludes the later addition of other digital/analog data environmental measurement devices such as solar irradiance sensors that may be needed to support new/emerging research interests.

An example of the problems pertaining to existing environmental monitoring sites can be illustrated through some recent work performed by one of the inventors of WISE-MP. During this effort, existing environmental severity data was gathered to infer a corrosion testing site's real-world conditions at Fort Drum, N.Y. The air pollution monitoring sites (ozone and sulfur dioxide) closest to Fort Drum, N.Y. were more than 50 miles apart from one another. In addition, the sulfur dioxide site itself was more than 45 miles from the test site. Both of these sites were managed by the New York Department of Environmental Conservation (DEC). The closest site that measures atmospheric chloride deposition data is more than 30 miles from the Fort Drum test site. This data was measured by the State University of New York—Oswego in support of the National Atmospheric Deposition Program. Weather data at Fort Drum was measured by the US Army. Each of these organizations collects their data for entirely different purposes and it is generally unavailable to the public for a lengthy period after it is measured. In addition, these group's existing databases are not coordinated or integrated. To compound these issues there is routinely a 6-12 month lag before air pollution and chloride deposition data is made available to the public. Detailed weather data is harder to obtain and usually requires support from monitoring agencies. Since the combined suite of environmental data is not measured at the exact site where engineering analyses are needed, such data does not accurately show the actual variable environmental conditions at other locations (in this case Fort Drum). A new approach to environmental characterization is needed to overcome the obvious limitations of this type of approach.

An application of this invention, a Weather Instrumentation and Specialized Environmental Monitoring Platform (WISE-MP), is to provide a small footprint, state-of-the-art, portable environmental monitoring system designed to automatically collect and wirelessly transmit comprehensive, real-world and near-to-real-time environmental severity data for specific locations of interest such as sites where material degradation predictions are needed for design and sustainability analysis purposes. The system combines commercially available instruments and related equipment to collect weather, air pollution, and atmospheric chloride data. It also has the built-in capability of supporting numerous additional sensors (digital and 0-5V analog) that can easily be incorporated into the system at a later date and as needed once deployed. The WISE-MP employs integrated data logging to consolidate the information gathered by all of the instruments and wireless communications (via cellular transmission) to transmit data to a database for archiving and access purposes. An IP camera is incorporated into the system to enable visual observations and inspection of test specimens and the monitoring equipment. This integrated approach allows for remote users to monitor system operation while quantifying the specific environmental conditions at the same time and place where exposure test specimens or assets are located. The WISE-MP also includes a test stand and rack used to expose material test specimens to the outdoor environment. The combination of environmental and test data enables the ability to construct highly precise materials degradation models. Once such models are created, WISE-MP may be used to collect the environmental data needed to support routine maintenance and related sustainment analyses in support of infrastructure and complex systems, including aircraft.

WISE-MP represents a new approach for collecting environmental data by integrating a full-range of commercial equipment in a single portable, small-footprint, integrated system. Unlike existing large, fixed monitoring systems, WISE-MP measures consolidated outdoor environmental severity and exposure data responsible for the numerous corrosion factors that affect the overall damage to critical assets and infrastructure. The system was designed to be extendible to facilitate the incorporation of additional environmental sensors and/or measurement devices. Its compact size enables easy movement from site to site and it was specifically designed to enable integrated data collection (from all monitoring equipment—present and future). Wireless communications and data transfer between WISE-MP and a remote database server will allow for data to be quickly collected, archived, backed-up, and made available to users. The capability of collecting environmental data in real time using a single small form factor system and subsequently transmitting the measurements wirelessly to a remote database server in real time demonstrates a significant advancement over existing practices and state-of-the-art.

The advantages of the WISE-MP invention includes the ability to directly measure accurate, site-specific environmental data that quantifies the variable outdoor environment. In addition, the integrated data gathering and wireless transmission capabilities minimizes the amount of human contact and intervention with the system, thus enabling a more automated processes. The WISE-MP system will allow for multi-site data gathering at near-to-real time with high-resolution of the data with nearly instantaneous access as it is acquired.

Figure 4:
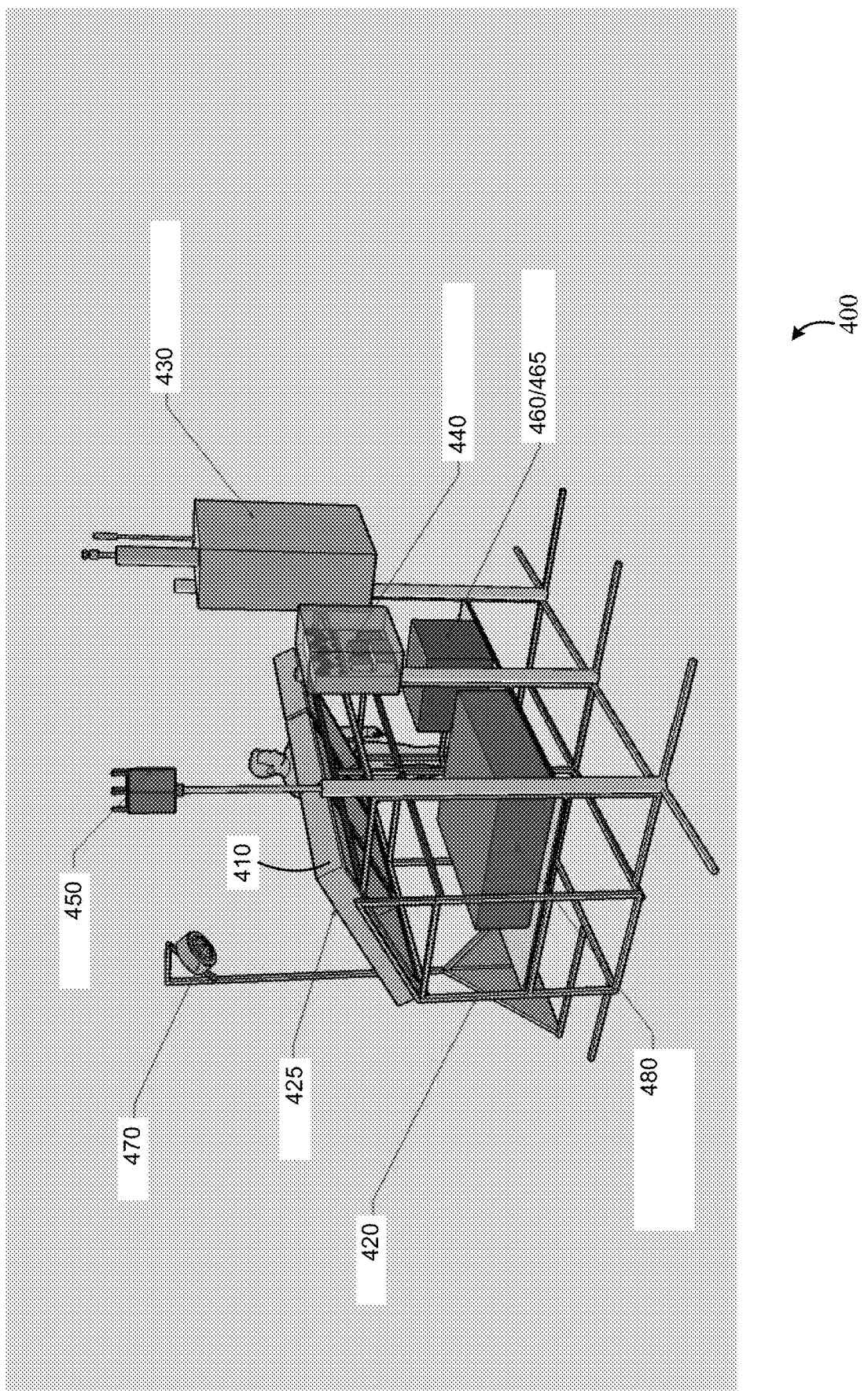
FIGS. 4-5 depict exemplary environmental monitoring platforms suitable for use in the system of FIG. 1.
Figure 5:
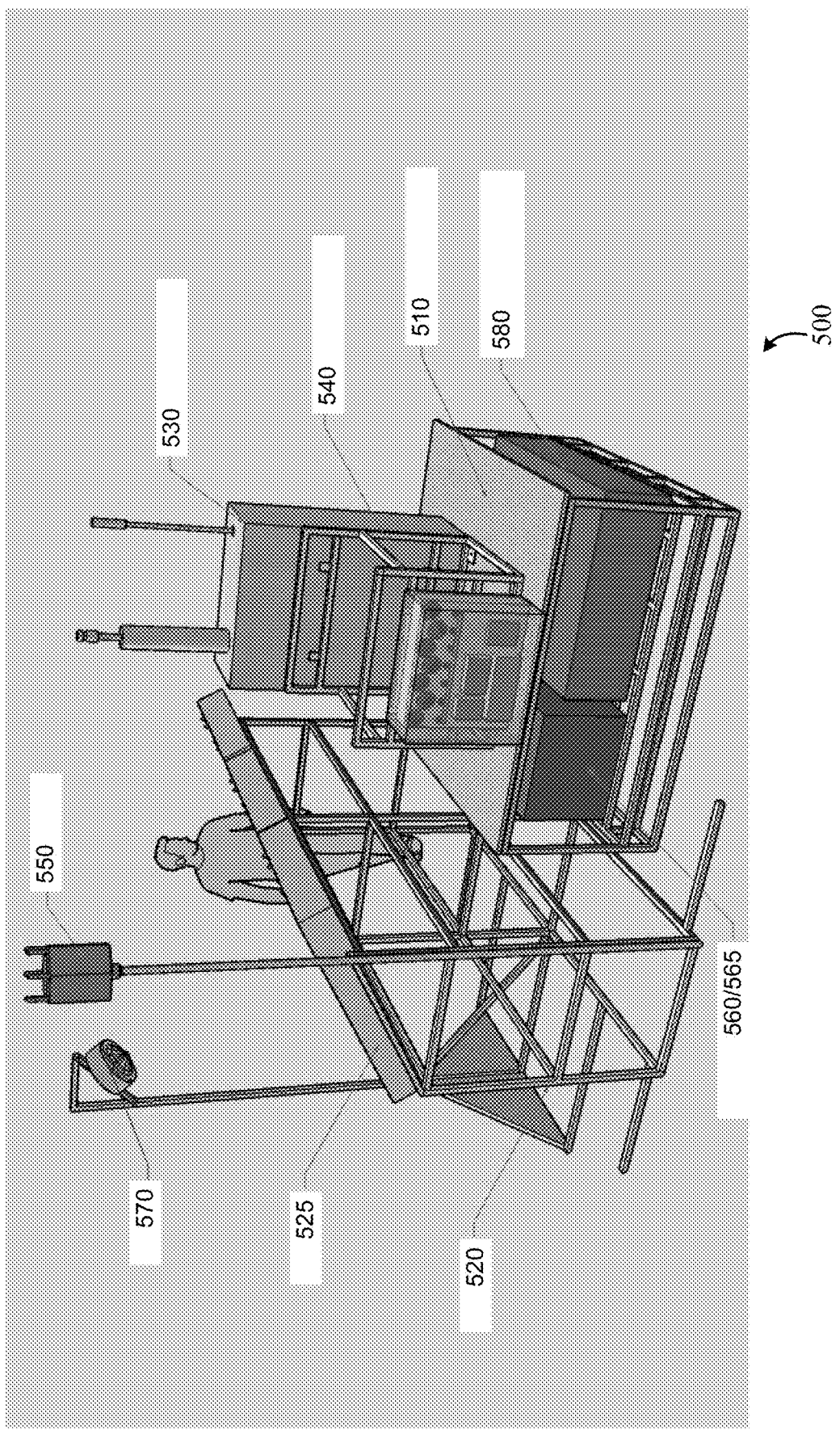

FIGS. 4-5 depict exemplary environmental monitoring platforms suitable for use in the system of FIG. 1. Specifically, referring to FIGS. 4-5 together, an exemplary WISE-MP may comprise, illustratively, seven major components; namely (1) an Environmental Monitoring Instrument Table 410/510; (2) a Sample Test Stand 420/520 and Rack 425/525; (3) an Ambient Air Quality Monitor 430/530; (4) a Chloride Deposition Monitor 440/540; (5) a Weather Station 450/550; (6) an Integrated System Controller 460/560 with an uninterruptible power supply (UPS) 465/565; and (7) a Sample Monitoring Camera 470/570.

An exemplary Environmental Monitoring Instrument Table 410/510 holds one or more weatherproof enclosures 480/580 that contain commercial equipment including the Ambient Air Quality Monitor 430/530, the Chloride Deposition Monitor 440/540 and the Integrated System Controller 460/560 components. A weather station 450/550 is also affixed to the table. The elevation above the ground is important for air sampling and gathering weather data so the table has two levels. The lower level of the table holds an integrated system controller and chloride deposition monitor enclosures while the upper level has a platform that holds the Ambient Air Quality Monitor and Weather Station. The table may be made of relatively lightweight materials with forklift slots to facilitate moving it from site to site. The other sub-systems can be removed with relative ease from the table for transport to other test locations.

An exemplary Sample Test Stand 420/520 and Rack 425/525 holds, illustratively, three modular specimen racks that are adjustable to allow for nearly any size test specimen to be attached for exposure. Racks may be angled at 30 Degrees and face southward to maximize exposure of test specimens to UV radiation. The racks may have nylon hardware that allows for isolation of test specimens from the base material of the rack itself. Depending on the location and orientation of the test table at the site, the Sample Test Stand and Rack can be joined to the Test Table itself or be separated. The Stand may be collapsible to allow for easy transport from site to site.

An exemplary Ambient Air Quality Monitor 430/530 may comprise, illustratively, a commercial system that consists of several complex instruments that are used to detect gaseous pollutants in the atmosphere. The system is modular in that a variety of sensors can be added to the platform if so desired depending on the value of that data and the pollutants of concern at a specific test site. The monitor may be mounted above the table on a stand to allow for air circulation for the heating and cooling systems used to keep the interior of the cabinet at operational temperatures. In various embodiments, a commercial or custom Ambient Air Quality Monitor configured to provide data to the system collects data relevant to the utilized corrosion damage model or framework, such as NO, NO2, NOx, O3, SO2, CO, H2S, Particulate Matter (e.g., PM10, PM4, PM2.5, and/or PM1), VOCs and/or other atmospheric criteria.

An exemplary Chloride Deposition Monitor 440/540 may comprise, illustratively, seven filter cartridges and solenoid valves with a flow controller and data logger to allow for each filter to be exposed individually to air brought in from the outside individually. The controller is easily programmable to allow for air to be collected over any duration of time. The purpose of this test instrument is to collect weekly atmospheric chloride deposition data. This component is the only instrument on WISE-MP that requires regular physical interaction, although other embodiments might not require regular physical interactions. At regular intervals (e.g., every 4-6 weeks), the filters are collected and analyzed to determine the amount of chloride aerosols in the atmospheric environment surrounding the WISE-MP. For example, initial samples may be retrieved every 6 weeks such that chloride concentration data will be at a weekly resolution level, but resolution can be adjusted up or down depending on need.

An exemplary Weather Station 450/550 may comprise, illustratively, a commercially procured item that is used to measure a variety of weather related data. It is mounted above the Ambient Air Quality Monitor approximately 12 feet above the ground level. In various embodiments, a commercial or custom Weather Station configured to provide data to the system collects data relevant to the utilized corrosion damage model or framework, such as Temperature, Relative Humidity, Air Pressure, Rainfall (e.g., short and long term accumulation), Rain Intensity (e.g., a running one minute average in 10 second steps, longer/shorter average, longer shorter steps etc.), Wind Speed (e.g., average, max, min), Wind Direction (e.g., azimuth, average, max, min etc.) and/or other weather-related criteria.

An exemplary Integrated Systems Controller 460/560 may comprise, illustratively, a weather-proof enclosure that contains a ruggedized laptop computer, router, electrical line conditioner and other network controllers and sensor interfaces. All other components of the WISE-MP connect to the Integrated Systems Controller via USB, RS-232 or CAT5/CAT6 cables via weather-tight connections through the case. Data for the sensor packages are gathered using the computer and Local Area Network housed within the Systems Controller. Diagnostics and data gathered from the instrumentation and sensors are collected and stored on the computer and transmitted from the computer to a separate database via 4G/LTE Cellular interface.

An exemplary Sample Monitoring Camera 470/570 may be located above and looking down on the Sample Test Stand and Rack so that samples can be monitored remotely as they are exposed to environmental conditions. The camera is of high enough quality to acquire high-quality images of samples, sample panels and the like to support respective evaluations of environmental performance. The camera is such that it can zoom in on and move side to side so it can view individual panels. The camera may be operated remotely via the LAN and cellular connection to the test platform.

The WISE MP structure may be composed of welded aluminum sections that are modular in design that allow for easy assembly with fasteners and fittings. The test stand supports the exposure rack, which may be angled at 30 degrees from the horizontal, and a stand on which the sample monitoring camera is mounted. The test table may be composed of welded aluminum box-shaped tubing supporting the aluminum diamond plate with an integrated shelf to hold the environmental monitors and systems controller. The footprint may be about 5 feet×5 feet with the table being approximately 4 feet tall. The Ambient Air Quality Monitor may sit on a stand 12 inches above the top of the table and the Weather Station may be approximately 2 feet above the top of the Ambient Air Quality Monitor.

Various embodiments of the WISE-MP may be used to collect data about actual corrosion test site environmental conditions via, illustratively, one or more corrosion test modules (CTM) 170 operably coupled to a platform 105 (e.g., via a cellular telephone or other interface) to provide thereto near-to-real time corrosion damage data associated with a specific site that be studied and utilized in modeling as well as in advanced laboratory environmental test chambers. Test stand and sample racks may hold samples that are exposed in that environment and can be studied after exposure wherein the data informs the user to what the test specimens have been exposed while at the test site.

Numerous other sensors may be feasibly added to the WISE MP and integrated into the system for automated data acquisition and upload to the database. The Ambient Air Quality Monitor does allow for modular change out of sensor packages so that CO, H2S, Particulate Matter (PM10, PM4, PM2.5, and PM1) and VOC sensors could be added with relative ease. Some of the sensors utilized in WISE-MP may be used, and are used for monitoring air pollution in highly populated or industrial work areas for the purposes of understanding air quality and its impact to human health. While the purpose and driving factor for this invention is to understand the environment to better predict corrosion in those environments, it is feasible that the WISE MP could be used to understand environments where it is placed for a variety of purposes.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A system, comprising:
    a plurality of ground-based environmental monitoring platforms (EMPs) disposed at respective geographic locations and configured to periodically gather local weather condition and atmospheric contaminant measurements to generate thereby time-stamped weather and contaminant data corresponding to each geographic area; and
    a ground-based management platform, configured to receive the time-stamped weather and contaminant data from each of the plurality of EMPs and responsively update accumulated degradation information of assets or components thereof;
    wherein each asset or component thereof has associated with it a respective accumulated corrosion damage profile (ACDP) defining respective accumulated amounts of exposure of the asset or component thereof to each of a plurality of weather conditions and atmospheric contaminants;
    wherein each asset has associated with it a respective time-location profile defining time periods during which the asset was located at any of a plurality of locations of interest including the plurality of EMP locations;
    said management platform being configured to identify those assets having a time-location history correlating with received EMP time-stamped weather and contaminant data;
    said management platform being configured to update each ACDP associated with an identified asset in accordance with a plurality of time-locations correlating to the received EMP time-stamped weather and contaminant data, wherein each asset or component thereof has associated with it a respective model corrosion damage profile (MCDP) defining at least one threshold level of accumulated amounts of exposure of the asset or component thereof to at least one of said plurality of weather conditions and atmospheric contaminants;
    said management platform being further configured to compare each updated ACDP to a corresponding MCDP to determine if a threshold level of accumulated amounts of exposure has been exceeded, and to generate an event indicator in response to said threshold level being exceeded.

2. The system of claim 1, wherein said plurality of weather conditions comprise any of temperature, pressure, humidity and insolation, and wherein said plurality of atmospheric contaminants comprise any of chlorides, ozone, sulfur dioxide and nitrogen oxides.

3. The system of claim 1, wherein the event indicator comprises a maintenance request.

4. The system of claim 1, wherein each asset comprises an aircraft, and each location of interest comprises an airfield or location therein.

5. The system of claim 1, wherein the MCDP of an asset or portion thereof is determined in accordance with design criteria.

6. The system of claim 1, wherein the MCDP of an asset or portion thereof is determined in accordance with a cumulative corrosion damage model (CCDM).

7. The system of claim 3, wherein the MCDP of an asset or portion thereof is adapted in response to empirical data indicative of corrosion factors outside the CCDM.

8. The system of claim 3, wherein the MCDP of an asset or portion thereof is adapted in response to analysis data generated after an indicated event.

9. The system of claim 1, wherein each EMP comprises:
    a plurality of sensors configured to measure respective weather conditions or atmospheric contaminant levels for a geographic location; and
    a computing device including a processor configured to encode a plurality of sensor measurements and a time stamp into a transport packet and to transmit that packet toward said management platform via a communications network.

10. The system of claim 1, wherein at least some of said EMPs receive additional measurements of weather conditions or atmospheric contaminant levels from local measurement equipment, said processor further configured to include the additional measurements of weather conditions or atmospheric contaminant levels within the transport packet.

11. The system of claim 10, wherein the local measurement equipment comprises any of local weather equipment, local atmospheric contaminant equipment and local defense sensor equipment.

12. The system of claim 1, wherein at least some of the EMPs comprise an Ambient Air Quality Monitor configured to monitor one or more of NO, $NO_2$, NOx, $O_3$, $SO_2$, CO, $H_2S$, Particulate Matter and VOCs.

13. The system of claim 12, wherein at least some of the EMPs comprise a Chloride Deposition Monitor and a Weather Station.

14. A computer implemented method for determining accumulated corrosive stresses experienced by an asset or component thereof, the method comprising:
    receiving time-stamped weather and contaminant data from one or more of a plurality of environmental monitoring platforms (EMPs), each EMP disposed at a respective geographic location and configured to periodically gather local weather condition and atmospheric contaminant measurements to generate thereby said time-stamped weather and contaminant data corresponding to that geographic location;
    identifying those assets having a time-location history correlating with received EMP time-stamped weather and contaminant data, wherein each asset or component thereof has associated with it a respective accumulated corrosion damage profile (ACDP) defining respective accumulated amounts of exposure of the asset or component thereof to each of a plurality of weather conditions and atmospheric contaminants;
    updating each ACDP associated with an identified asset in accordance with at least a time-location correlating with the received EMP time-stamped weather and contaminant data.

15. The computer implemented method of claim 14, wherein said plurality of weather conditions comprise any of temperature, pressure, humidity and insolation; and wherein said plurality of atmospheric contaminants comprise any of chlorides, ozone, sulfur dioxide and nitrogen oxides.

16. The computer implemented method of claim 14, wherein each asset or component thereof has associated with it a respective model corrosion damage profile (MCDP) defining at least one threshold level of accumulated amounts of exposure of the asset or component thereof to at least one of said plurality of weather conditions and atmospheric contaminants, said method further comprising:
  comparing each updated ACDP to a corresponding MCDP to determine if a threshold level of accumulated amounts of exposure has been exceeded, and to generate an event indicator in response to said threshold level being exceeded.

17. The computer implemented method of claim 16, wherein the MCDP of an asset or portion thereof is determined in accordance with at least one of design criteria and a cumulative corrosion damage model (CCDM), and wherein the MCDP of an asset or portion thereof is adapted in response to at least one of empirical data indicative of corrosion factors outside the CCDM, and analysis data generated after an indicated event.

18. An apparatus for determining accumulated corrosive stresses experienced by an asset or component thereof, the apparatus comprising a processor configured for:
  receiving time-stamped weather and contaminant data from one or more of a plurality of environmental monitoring platforms (EMPs), each EMP disposed at a respective geographic location and configured to periodically gather local weather condition and atmospheric contaminant measurements to generate thereby said time-stamped weather and contaminant data corresponding to that geographic location;
  identifying those assets having a time-location history correlating with received EMP time-stamped weather and contaminant data, wherein each asset or component thereof has associated with it a respective accumulated corrosion damage profile (ACDP) defining respective accumulated amounts of exposure of the asset or component thereof to each of a plurality of weather conditions and atmospheric contaminants;
  updating each ACDP associated with an identified asset in accordance with at least a time-location correlating with the received EMP time-stamped weather and contaminant data.

19. A tangible and non-transient computer readable storage medium storing computer-executable instructions which, when executed by a system of computer processors, adapt the operation of the system for:
  determining accumulated corrosive stresses experienced by an asset or component thereof, the method comprising:
  receiving time-stamped weather and contaminant data from one or more of a plurality of environmental monitoring platforms (EMPs), each EMP disposed at a respective geographic location and configured to periodically gather local weather condition and atmospheric contaminant measurements to generate thereby said time-stamped weather and contaminant data corresponding to that geographic location;
  identifying those assets having a time-location history correlating with received EMP time-stamped weather and contaminant data, wherein each asset or component thereof has associated with it a respective accumulated corrosion damage profile (ACDP) defining respective accumulated amounts of exposure of the asset or component thereof to each of a plurality of weather conditions and atmospheric contaminants;
  updating each ACDP associated with an identified asset in accordance with at least a time-location correlating with the received EMP time-stamped weather and contaminant data.

* * * * *